United States Patent [19]

Mack et al.

[11] Patent Number: 4,816,418
[45] Date of Patent: Mar. 28, 1989

[54] METHOD AND APPARATUS FOR PERFORMING AUTOMATED, MULTI-SEQUENTIAL IMMUNOASSAYS

[75] Inventors: Daniel R. Mack, Half Moon Bay; Michael G. Konicek, Cupertino, both of Calif.

[73] Assignee: Sequoia-Turner Corporation, Mountain View, Calif.

[21] Appl. No.: 757,676

[22] Filed: Jul. 22, 1985

[51] Int. Cl.$^4$ .................. G01N 35/00; G01N 35/02; G01N 35/06
[52] U.S. Cl. .......................... 436/518; 422/65; 422/69; 436/548; 436/800; 436/808
[58] Field of Search ............... 436/800, 808, 518, 548; 422/65, 69

[56] References Cited

U.S. PATENT DOCUMENTS

| | | | |
|---|---|---|---|
| 3,951,605 | 4/1976 | Natelson | 436/808 X |
| 4,128,628 | 12/1978 | Brooker | 436/808 X |
| 4,219,530 | 8/1980 | Kopp | 422/69 |
| 4,265,855 | 5/1981 | Mandle | 422/65 |
| 4,271,123 | 6/1981 | Curry | 436/800 X |
| 4,299,796 | 11/1981 | Esch | 422/65 X |
| 4,383,041 | 5/1983 | Kutsusawa | 436/800 X |
| 4,628,026 | 12/1986 | Gardell | 436/808 X |

Primary Examiner—Sidney Marantz
Attorney, Agent, or Firm—Limbach, Limbach & Sutton

[57] ABSTRACT

Methods and apparatus useful in automated performance of immunoassays, in some preferred embodiments, relying upon the sandwich immunoassay technique, are described. Each rack of reaction tubes is uniquely identified by an optical identifier disc which is read by the automatic controller. The assays are performed at two stations which configuration thereby permits arrays to be run on a second rack of reaction tubes while the first rack is in process. The cooperation of the identifier disc and the automatic controller minimizes operator error and helps improve the reliability of the data obtained.

15 Claims, 24 Drawing Sheets

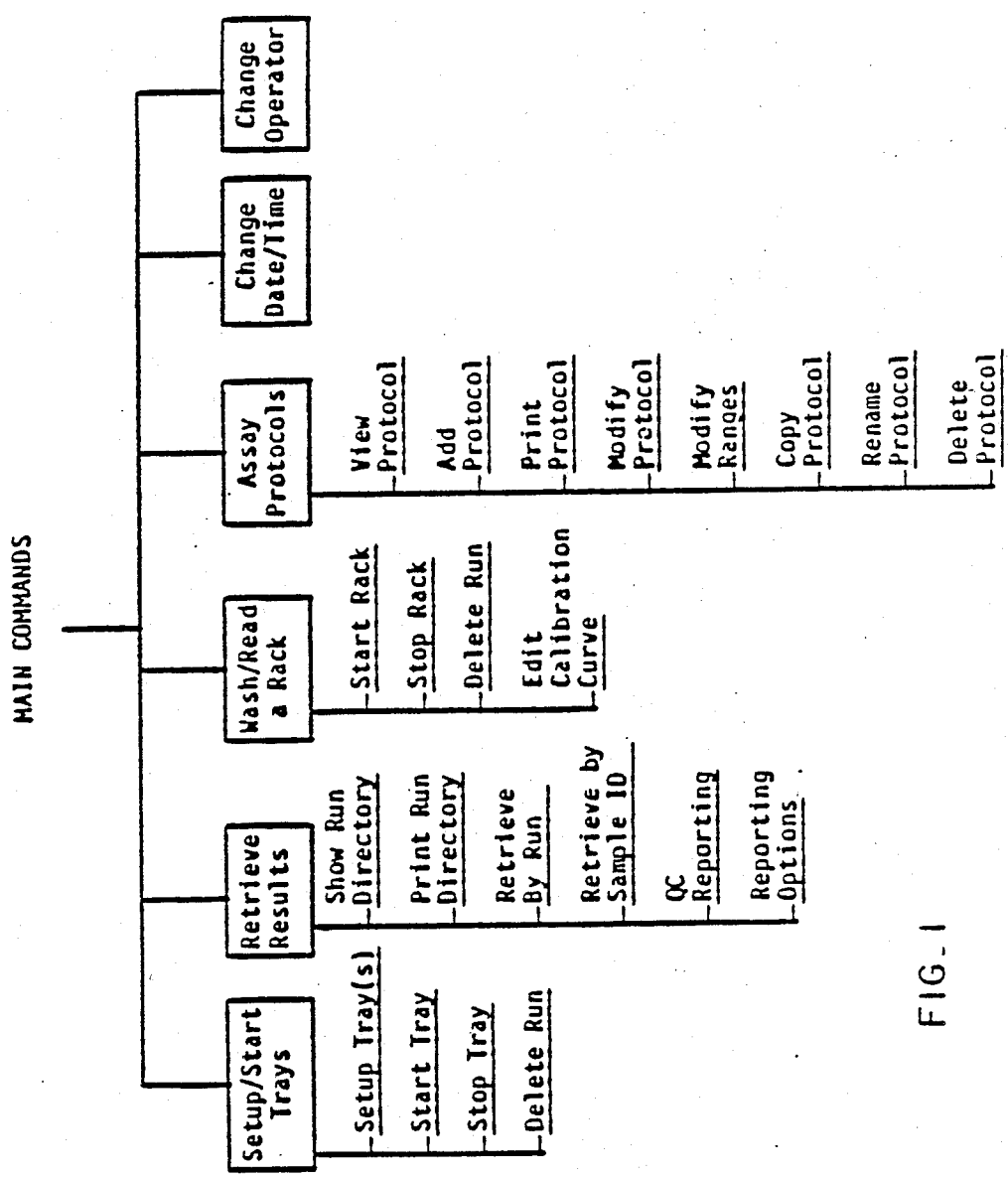
FIG_1

| Date: 05-07-85 | MAIN COMMANDS | Time: 10:22:14 |
|---|---|---|
| Operator: Smith | | Version: 1.0 |

| Sample Processor | Waste | Reaction Processor |
|---|---|---|
| Running HCG-E | [OK] | Ready |
| Run 88   Rack D | Wash [OK] | |
| [Sample 1]  [Tube 2] | Quench [OK] | [Empty] |

<Select Function>

<<F1   Retrieve Results        F2>> Set Up/Start Tray(s)
<<F3   Change Date/Time        F4>> Wash/Read a Rack
<<F5                           F6>> Assay Protocols
<<F7                           F8>> Change Operator
<<F9   HELP                    F0>>

FIG_2

```
DATE: 05-03-85           ASSAY SELECTION              TIME: 16:11:40

┌───────┐
  │ HCG-E │    CEA-E         CKMB-E           AFP-E
  └───────┘
    FER-E      PSA-E         TSH-E

IgE-E         PRL-E            PAP-E

<Highlight desired assays, then Select Function>

Show Protocol      <<F1| F2>>    Add Protocol
  Print Protocol     <<F3| F4>>    Delete Protocol
  Rename Protocol    <<F5| F6>>    Modify Protocol
  Copy Protocol      <<F7| F8>>    Modify Values/Ranges
  HELP               <<F9| F0>>    Main Commands
```

FIG. 3

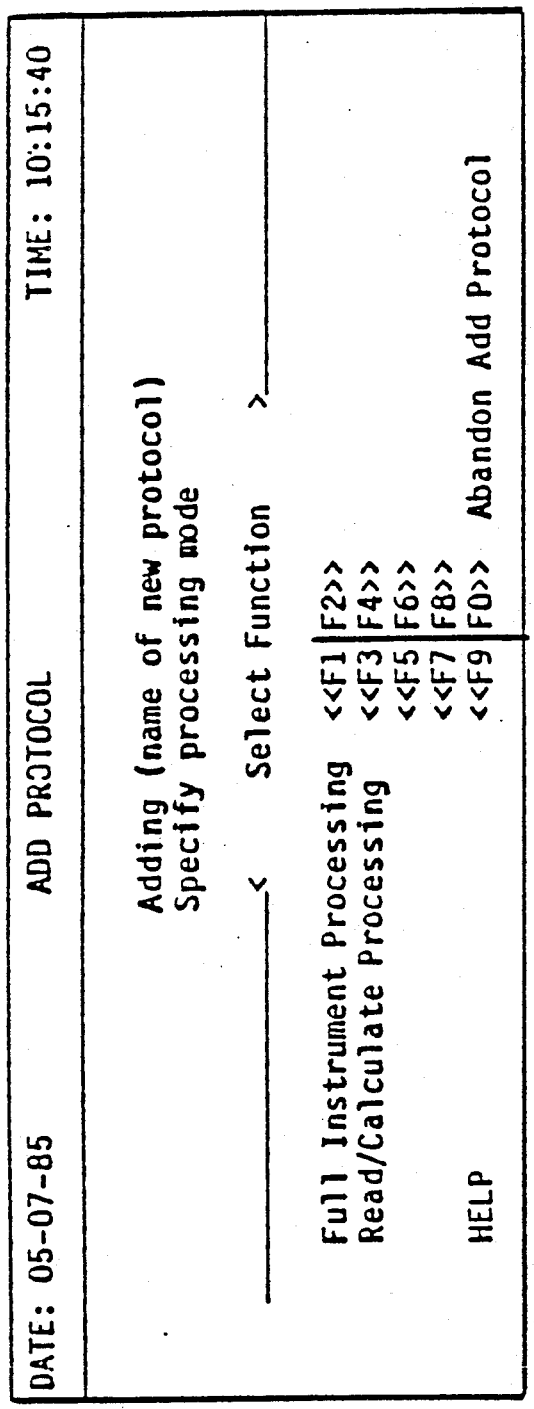
FIG_4

```
DATE: 05-07-85  ADD PROTOCOL        TIME: 16:19:53

First Incubation:              Second Incubation:

┌─────────────────────────┬─────────────────────────────┐
│ SAMPLE PROCESSOR        │ REACTION PROCESSOR          │
│                         │                             │
│ Addition Order:         │ Curve Type:                 │
│ N of Calibrators:       │ Units:                      │
│ N of Controls:          │ Optics Mode:                │
│                         │                             │
│                         │ Primary:                 nm │
│ Sample Vol. Conjugate Vol. │ Secondary:            nm │
│  [    ]      [    ]     │                             │
└─────────────────────────┴─────────────────────────────┘

<Enter protocol parameters>

<<F1>  <<F2>>  Undo Changes
       <<F3>> <<F4>>
       <<F5>> <<F6>>  Modify Values/Ranges
       <<F7>> <<F8>>  Store Altered Protocol
HELP   <<F9>> <<F0>>  Abandon Changes Made to Protocol
```

FIG - 5

```
DATE: 05-07-85      ADD PROTOCOL      TIME: 10:15:85

Calibrator Values         Control Ranges          Patient Ranges

Number:  Values           ID  Low  High           - Reference Range-
                                                     Low  High
    1:
    2:                                            - CV% Limit -
    3:
    4:                                            - Max. Conc. -
    5:
    6:
                          Control Reps:           Sample Reps:
Calibrator Reps.

Values and Ranges for _____
              <Enter Protocol Parameters>

<<F1| F2>> Undo Changes
      <<F3| F4>>
      <<F5| F6>> Modify Protocol
      <<F7| F8>> Store Altered Protocol
HELP  <<F9| F0>> Abandon Changes Made to Protocol
```

FIG_6

```
┌─────────────────────────────────────────────────────────────┐
│  DATE: 05-07-85  ADD PROTOCOL        TIME: 10:15:40         │
│                                                              │
│  ┌──────────────────────┬──────────────────────────────┐   │
│  │ SAMPLE PROCESSOR     │ REACTION PROCESSOR           │   │
│  │                      │                              │   │
│  │ N of Calibrators:    │ Curve Type:                  │   │
│  │ N of Controls:       │       Units:                 │   │
│  │                      │ Optics Mode:                 │   │
│  │                      │                              │   │
│  │                      │   Primary:              nm   │   │
│  │                      │ Secondary:              nm   │   │
│  │                      │                   ┌──────┐   │   │
│  │                      │                   │      │   │   │
│  │                      │                   └──────┘   │   │
│  └──────────────────────┴──────────────────────────────┘   │
│                        Adding XYZ                            │
│       <Enter new parameters or Select Function>              │
│  ─────────────────────────────────────────────────────────  │
│       <<F1 | F2>>  Undo Changes                              │
│       <<F3   F4>>                                            │
│       <<F5   F6>>  Modify Values/Ranges                      │
│       <<F7   F8>>  Store Altered Protocol                    │
│       <<F9   F0>>  Abandon Changes Made to Protocol          │
│              HELP                                            │
└─────────────────────────────────────────────────────────────┘
```

FIG – 7

```
DATE: 05-07-85    ASSAY SELECTION    TIME: 10:14:22

Run 8 : Setup a New Run

Run 7 : TANDEM HCGQUAL
        Run 6 : TANDEM-E IGE
        Run 5 : TANDEM-E HCG
        Run 4 : TANDEM-E AFP
        Run 3 : TANDEM-E IGE
        Run 2 : TANDEM-E IGE

- Sample Processor -

Run 2 : TANDEM-E IGE   Tray 2

<Highlight desired Run then Select Function>
SETUP TRAY(S)   <<F1    F2>>  (START TRAY)
                <<F3    F4>>  (STOP TRAY)
                <<F5    F6>>
                <<F7    F8>>  DELETE THIS RUN
        HELP    <<F9    F0>>  MAIN COMMANDS
```

FIG_8

```
DATE: 05-07-85   SETUP/START TRAY(S)   TIME: 10:14:22

TANDEM-E HCG     TANDEM-E CKMB    TANDEM-E PAP
TANDEM-E HGH     TANDEM-E LH      TANDEM-E AFP
TANDEM-E FERR    TANDEM-E IgE     TANDEM-E TSH

Run 8 : Setup a New Run

<Highlight Protocol for this Run then Select Function>
 ENTER # OF TRAYS   <<F1    F2>>   CANCEL NEW RUN
                    <<F3    F4>>
                    <<F5    F6>>
                    <<F7    F8>>
           HELP     <<F9    F0>>   MAIN COMMANDS
```

| DATE: 05-07-85 | SETUP/START TRAY(S) | | TIME: 10:14:22 |

Run 8 : TANDEM FERR

| 1 | 0 mIU/ml | 2 | 200 mIU/ml | 3 | CONTROL 1 | 4 | CONTROL 2 | 5 | CONTROL 3 |
|---|---|---|---|---|---|---|---|---|---|
| 6 | Smith,D | 7 | Wallace,H | 8 | Kennedy,A | 9 | Lester,B | 10 | Kendall,B |
| 11 | | 12 | | 13 | | 14 | | 15 | |
| 16 | | 17 | | 18 | | 19 | | 20 | |
| 21 | | 22 | | 23 | | 24 | | 25 | |
| 26 | | 27 | | 28 | | 29 | | 30 | |
| 31 | | 32 | | 33 | | 34 | | 35 | |
| 36 | | 37 | | 38 | | 39 | | 40 | |
| 41 | | 42 | | 43 | | 44 | | 45 | |
| 46 | | 47 | | 48 | | 49 | | 50 | |
| 51 | | 52 | | 53 | | 54 | | 55 | |
| 56 | | 57 | | 58 | | 59 | | 60 | |

<Manually Enter sample IDs or Select Function>

| ASSIGN AUTO-IDs | <<F1 | F2>> | Setup/Start Tray(s) |
| SHOW NEXT TRAY | <<F3 | F4>> | |
| PRINT this TRAY | <<F5 | F6>> | CLEAR current SAMPLE |
| SHOW REACTION RACK | <<F7 | F8>> | CLEAR entire TRAY |
| HELP | <<F9 | F0>> | MAIN COMMANDS |

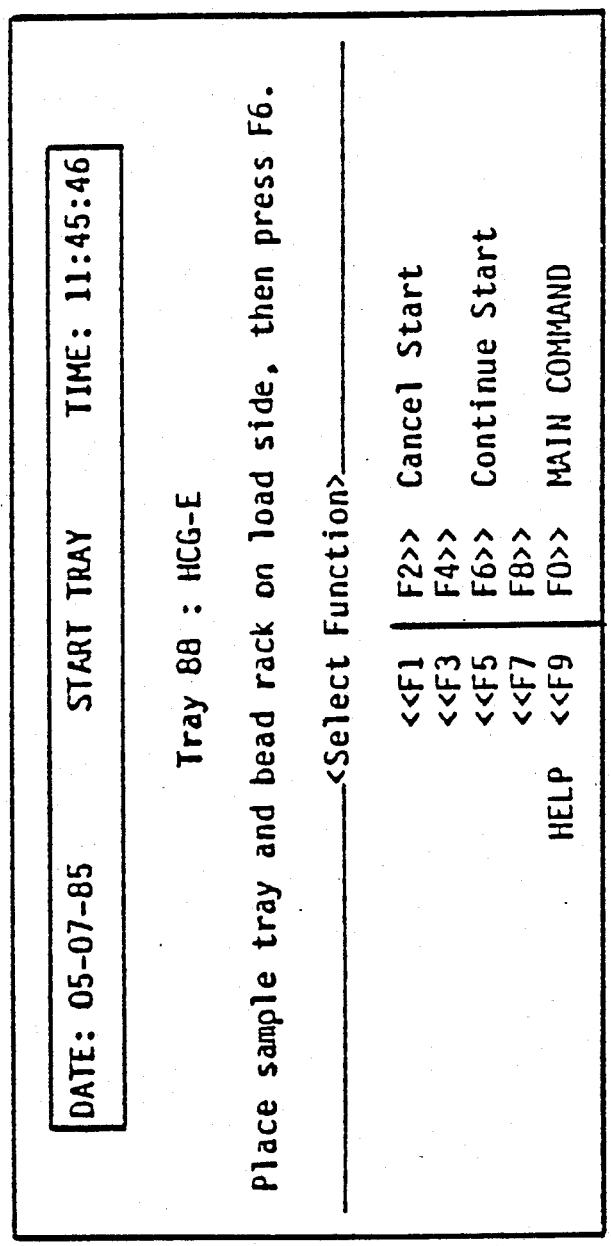
FIG._11

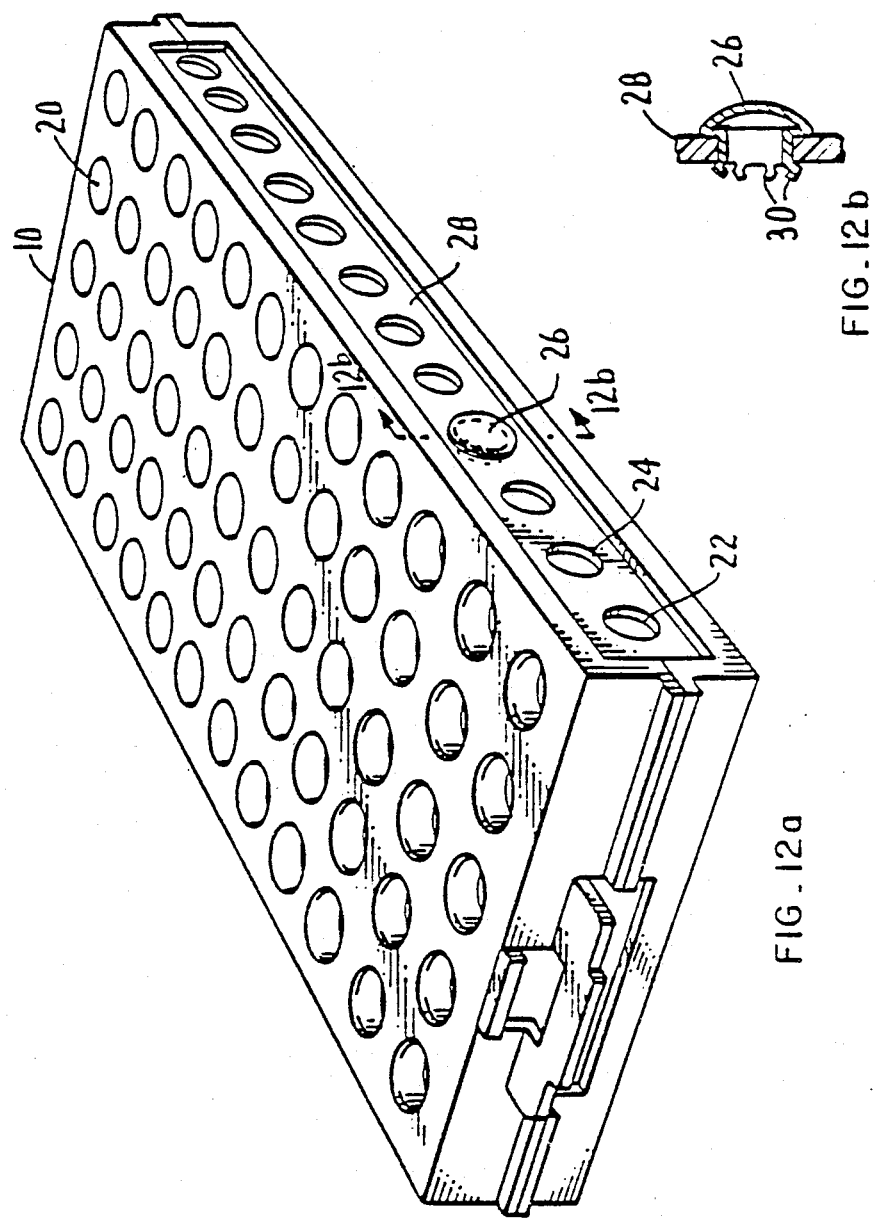
FIG._12a
FIG._12b

| DATE: 05-07-85 | MAIN COMMANDS | | TIME: 11:50:46 |
|---|---|---|---|
| Operator: | B# (sample ID) | | Version 1.1 |
| Sample Processor | Waste | | Reaction Processor |
| Running HCG-E | [OK] Wash [OK] Quench [OK] [OK] | | Ready |
| Run 85 Rack D | | | |
| sample \| tube | | | |

<Select Function>

| <<F1>> Retrieve Results | <<F2>> Setup/Start Trays |
|---|---|
| <<F3>> | <<F4>> Wash/Bead A Rack |
| <<F5>> | <<F6>> Assay Protocols |
| <<F7>> Change Date/Time | <<F8>> Change Operator |
| <<F9>> HELP | <<F0>> |

FIG.\_13

| DATE: 05-07-85 | | WASH/READ RACK | TIME: 11:50:46 |
|---|---|---|---|
| | | DS | |
| Run | Assay Protocol | Rack | Run Status | Washing/Reading Scheduled For |
| 91 | HCG-E | | Set Up | |
| 90 | HCG-E | | Set Up | |
| 89 | HCG-E | | Set Up | |
| 88 | HCG-E | D | Finished | |
| 67 | CEA-E/D | H | Incubating | 19:32 |

<Highlight desired run, the select function>

```
                       F1     F2>>   (Start Rack)
                       F3     F4>>   (Stop Rack)
                       F5     F6>>   Delete this Run
Edit Calibration Curve F7     F8>>   MAIN COMMANDS
                 HELP  F9     F0>>
```

FIG._14

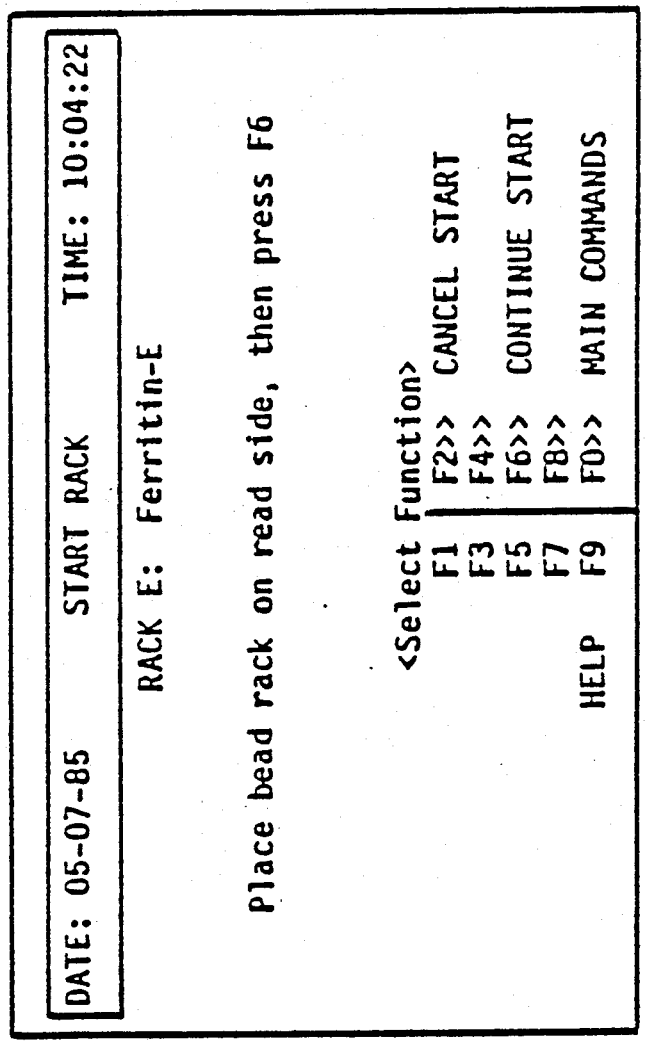
FIG_15

| DATE: 05-16-85 | MAIN COMMANDS | TIME: 17:15:40 |
|---|---|---|
| Operator: | | Version 1.1 |

| Sample Processor | Waste | Reaction Processor |
|---|---|---|
| Ready | [OK] [OK] Wash [OK] Quench [OK] | Running Ferritin-E Priming Run 101 Rack D [ empty ] |
| [Empty] [Empty] | | |

<Select Function>

| <<F1>> Retrieve Results | <<F2>> Setup/Start Trays |
|---|---|
| <<F3>> | <<F4>> Wash/Bead A Rack |
| <<F5>> | <<F6>> Assay Protocols |
| <<F7>> Change Date/Time | <<F8>> Change Operator |
| <<F9>> HELP | <<F0>> |

FIG.-16

```
DATE: 05-07-85    RETRIEVE RESULTS    TIME: 10:14:22

<<Run Storage Summary>>

Results from : 01-01-85 @ 08:00 to : 05:07:85 @ 15:33

Number of Runs  : 14        Number of Samples: 1011
Number of Trays : 37        Number of Tubes  : 2342

─────────────<Select Function>─────────────
Show Run Directory   <<F1    F2>> RETRIEVE RESULTS BY RUN
                     <<F3    F4>> RETRIEVE RESULTS BY SAMPLE ID
Print Run Directory  <<F5    F6>> QUALITY CONTROL REPORTS
                     <<F7    F8>> SETUP REPORTING OPTIONS
              HELP   <<F9    F0>> MAIN COMMANDS
```

FIG._17

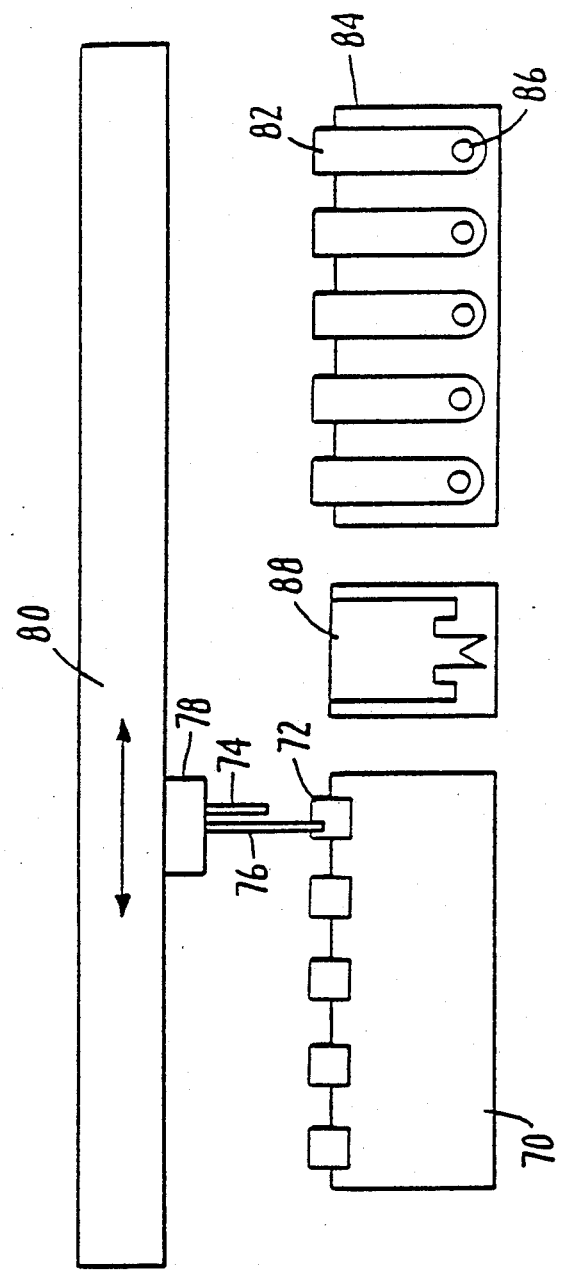
FIG._19

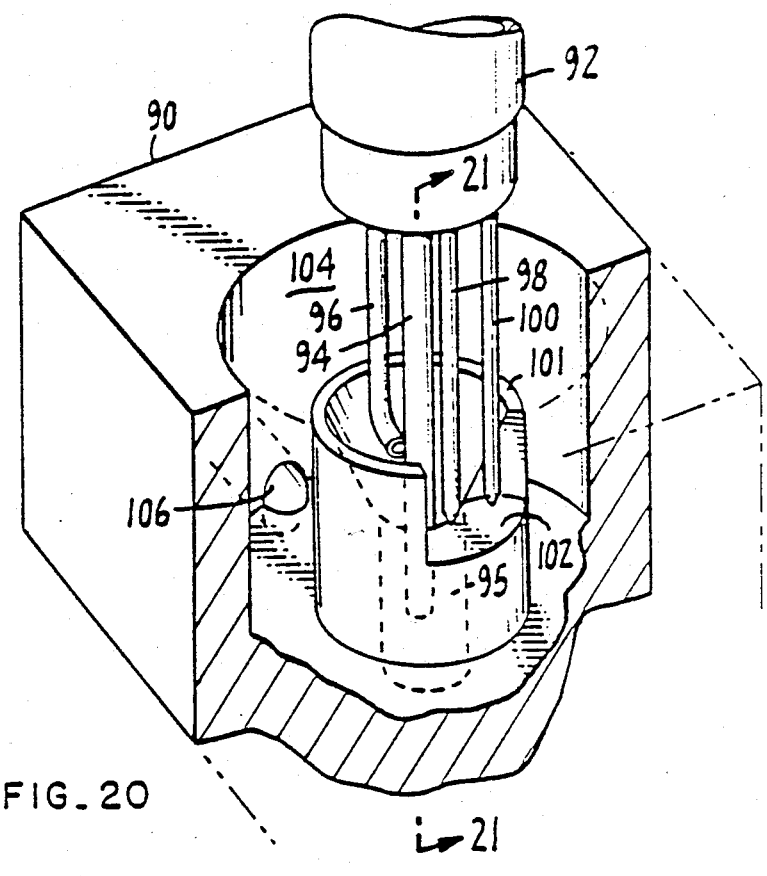
FIG_20
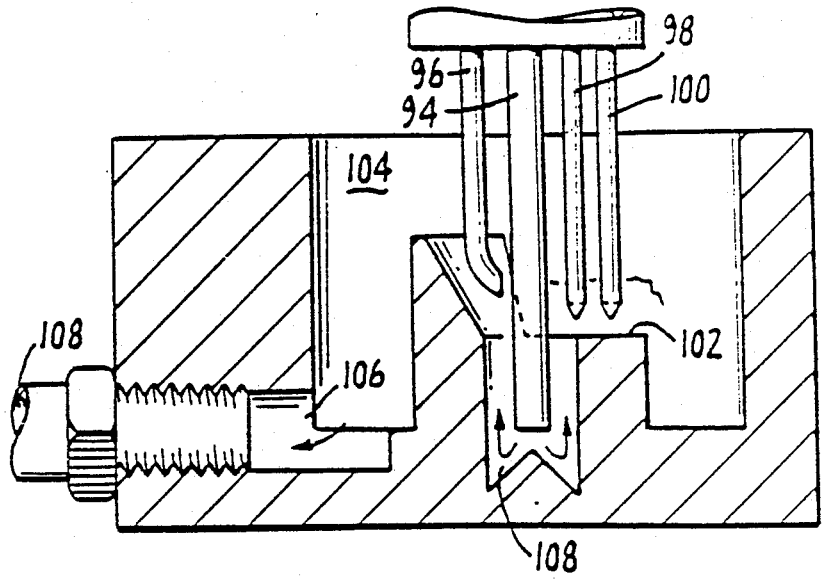
FIG_21

METHOD AND APPARATUS FOR PERFORMING AUTOMATED, MULTI-SEQUENTIAL IMMUNOASSAYS

DESCRIPTION

1. Technical Field

This invention relates generally to methods and apparatus useful in the automated performance of immunological assays and, more specifically, to methods and apparatus which permit nearly simultaneous and/or sequential processing of samples to determine photometrically or fluorometrically the presence and the concentration of specific antigens or antibodies in these samples.

2. Background of the Invention

Immunoassays have been recognized as useful in diagnosing, treating and immunizing mammals against pathogens. The development of monoclonal antibodies which inherently avoid the naturally heterogeneous response to antigens found in mammals has enabled a precise and accurate method for determining the presence and concentrations of specific antigens and antibodies in mammalian fluid samples. The automation of such immunoassay techniques based on monoclonal antibodies has not progressed rapidly due to at least two major problems. First, the known immunoassay techniques are extremely sensitive and require wash steps which are efficient to the parts per million level. This requirement makes the washing steps difficult to efficiently automate as a result of the time involved in the washing step and the rigid specifications covering impurities and contaminants. The use of common probes permits cross-contamination between samples, presenting yet another problem. Thirdly, immunoassay techniques require incubation periods for the completion of immunochemical reactions including the measurable result-determining step, e.g., the formation of an optically readable chromophore. These incubation periods introduce long periods of instrument unavailability.

One response to these lengthy incubation periods has been to remove a series of samples from the instrumentation during the incubation periods, then later returning them to the instrument for subsequent steps of the assay procedure. This solution has several drawbacks, making its widescale application unlikely. The extremely sensitive nature of immunoassay techniques requires that the reagents be added at the same time for calibration samples and unknown samples. Otherwise, the assay results are likely to skew. Thus, unsupervised removal of the samples, and reliance upon the operator's attention and diligence to accurately time and execute the necessary steps could lead to unacceptable confidence levels in the test results, diminishing the utility of the particular immunoassay technique.

Additionally, the possibility of running several different immunoassay techniques nearly simultaneously, or sequentially, introduces additional sources of error, again diminishing the confidence level anticipated for such immunoassay techniques. For example, if one series of samples were subjected to HCG immunoassay and another series of samples were subjected to CKMB immunoassay, at least two major errors could be made which could negate the results of either technique. First, the wrong reagents could be introduced to the sample at any time during the procedure. More probable, however, is the introduction of the wrong reagents after the incubation period.

Another error introducing potentially, statistically significant deviation into the immunoassay is derived from operator-generated imprecision in the timing of the incubation period. If the reactions are not always incubated for the same period of time, consistent and predictable results for different runs of the same immunoassay technique are less probable.

To address many of these obstacles to automated performance of immunoassays, the instant invention provides methods and apparatus which uniquely identify a rack of reaction tubes and relate that identity to the specific immunoassay technique to be performed on that rack. Further, the methods and apparatus provide for two stations which permit incubation to occur at an intermediate position between the stations. This configuration thereby permits several racks of samples to be run nearly simultaneously or sequentially. The machine-readable unique identification affixed to each rack prevents the addition of the wrong reagents to the samples and permits prompting of the operation by the apparatus to return a particular rack at the end of its incubation period.

It is therefore an object of this invention to provide a method for automatically performing immunoassay techniques on a series of reaction tube racks.

It is another object of this invention to provide a method for analyzing at least two racks of reaction tubes by the same immunoassay technique, starting the second rack while the first rack is in process.

It is a still further object of this invention to provide a method for analyzing reaction tubes by at least two different immunoassay techniques, starting the second rack while the first rack is in process.

It is yet another object of this invention to provide methods and apparatus for performing immunoassays on serum samples with precise timing to provide statistically significant levels of confidence, permitting their use and application in a clinical environment for diagnosis and therapy.

SUMMARY OF THE INVENTION

The methods and apparatus of this invention provide for the automation of immunoassay procedures wherein each rack of reaction tubes is uniquely identified. In one embodiment that identity is also manually communicated to an automatic controller simultaneously with a designation of the immunoassay technique to be performed. One specific embodiment of the way in which a rack is uniquely identified is disclosed wherein an optical identifier disc is fastened to an external wall of the reaction tube rack in one of twelve possible positions. The location of this disk can be optically sensed by the automatic controller.

The methods and apparatus utilize two processing stations during the procedure. At the first station sample serums are introduced to the reaction tubes and then reagents are provided which are useful in forming site specific antigen-antibody bonds. The reaction tube rack is then removed to an intermediate position where the samples are incubated for a period of time. The rack is loaded to a second station near the end of the first incubation period. In one embodiment, the automatic controller prompts the operator to load a specific rack as its first incubation period nears its end. Once loaded to the second station, the controller verifies the unique identity of that rack and then proceeds to perform the additional steps of the immunoassay protocol, including the formation of the result-determining characteristic, e.g., a chromophore or fluorescent body.

Some of the specific immunoassays which are described with reference to the method and apparatus of this invention are capable of detecting the presence of HCG (human chorionic gonadotropin), IgE (immunoglobulin Type E), FER (ferritin), CKMB (creatine kinase-MB), TSH (thyroid stimulating hormone), and AFP (alpha fetoprotein).

DESCRIPTION OF THE DRAWINGS

FIG. 1 is the MAIN COMMANDS Menu.
FIG. 2 is a first MAIN COMMANDS screen.
FIG. 3 is a first ASSAY SELECTION screen.
FIG. 4 is a first ADD PROTOCOL screen.
FIG. 5 is a second ADD PROTOCOL screen, prompting for entry of protocol parameters.
FIG. 6 is a third ADD PROTOCOL screen.
FIG. 7 is a fourth ADD PROTOCOL screen.
FIG. 8 is an ASSAY SELECTION screen.
FIG. 9 is a first SETUP/START TRAY screen.
FIG. 10 is a second SETUP/START TRAY screen.
FIG. 11 is a START TRAY screen.
FIG. 12a is a perspective view of the optical identifier disc located on the reaction tube rack.
FIG. 12b is a detailed view of the disc.
FIG. 13 is a MAIN COMMANDS screen displaying an output different than shown in FIG. 2.
FIG. 14 is a WASH/READ RACK screen.
FIG. 15 is a START RACK screen.
FIG. 16 is a MAIN COMMANDS screen with output different than shown in FIG. 2 or FIG. 13.
FIG. 17 is a RETRIEVE RESULTS screen.
FIG. 19 is an end view of the sample processor module, including a sample and conjugate probe.
FIG. 20 is a perspective view of a sample and conjugate probe wash station, partially broken away.
FIG. 21 is a side cross section view of the sample and conjugate probe wash station of FIG. 20.

DETAILED DESCRIPTION OF THE INVENTION

A. Immunoassay Techniques

Figure 18:
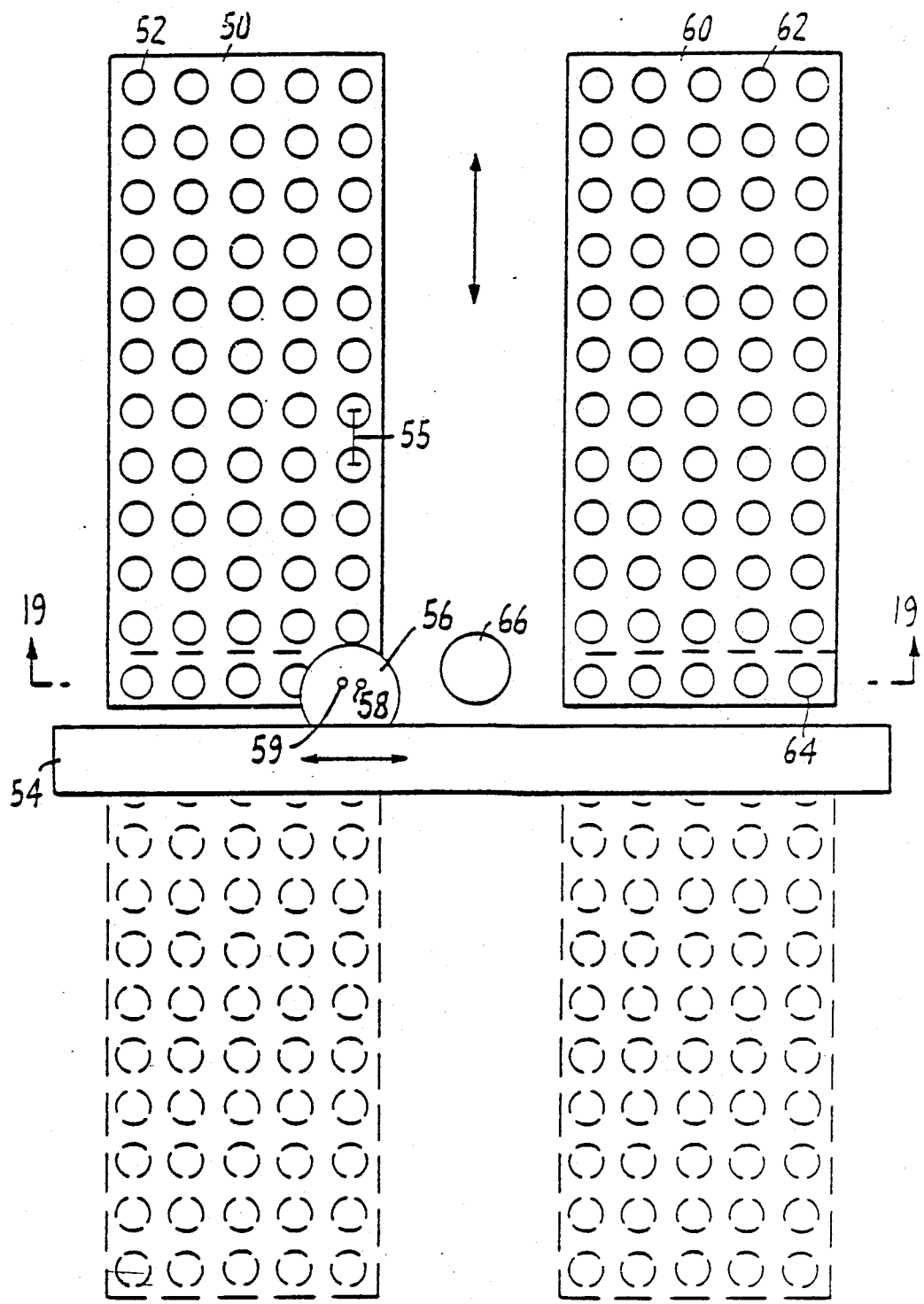
FIG. 18 is a top view of the sample processor module.

The methods and apparatus described herein are used to automatically perform the steps common to many immunoassay techniques. With no intention of limiting the scope of this invention to the particular embodiments described herein, a description of the techniques utilized in "two-site" or "sandwich" immunoassays is provided for background to the methods and apparatus of this invention. It is also intended to be within the scope of this invention to perform immunoassay techniques according to the methods and apparatus of this invention which do not utilize a solid support to bind to the antigen or antibody. Further, even though the specific embodiment described herein provides two processing stations within a single instrument, the separation of these two processing stations into two different modules or instruments is intended to be within the scope of this invention.

"Sandwich" immunoassays utilizing monoclonal antibodies are described in U.S. Pat. Nos. 4,361,647 and 4,376,110. The relevant portion of the disclosures therein are incorporated into the present application by this reference.

These "sandwich" immunoassays involve a technique in which an antigen layer is interposed between an unlabeled antibody substrate layer and a labeled antibody overlayer. These sandwich tests have been commonly used as a diagnostic tool to detect the presence of antigens in body fluids. To assay a sample of body fluid for the presence of a specific antigen, an antibody capable of recognizing and binding to an antigenic determinant of that antigen is adsorbed on a solid surface. The subject sample is applied to the antibody. The next step is the addition of a labeled antibody capable of recognizing and binding to a second antigenic determinant on the antigen or to the antigen-antibody complex already formed. The labeling may take the form of some type of radioactive isotope, a photoactive compound or chromophore-forming compound, or a compound which fluoresces. Further, it may be the circumstance where the "labeled" antibody is actually a catalyst or enzyme which can react with a substrate to form a chromophore. The sample, antibody and labeled antibody are then incubated for a suitable period of time. At the end of that first incubation period, a wash step is provided to remove non-adsorbed components from any antigen-antibody complexes which have formed.

The presence of labeled antibody, or of its measurable substrate effects, is then determined according to the type of labeling utilized, e.g., spectrophotometrically or spectrofluorometrically. A positive determination indicates that antigen was present in the test sample fluid. Quantitative determinations of the amount of antigen present in the test sample are made possible by comparison to characteristic intensity curves derived from assays utilizing known concentrations of antigen. It will be understood by those skilled in the art that immunoassay techniques are not limited to the antibody-antigen-antibody technique described herein. Other techniques using equally reliable immunogenic components, e.g., antibody-antibody-antibody reactions, are intended to be within the scope of this invention.

The sensitivity of this "sandwich" assay technique is adversely affected by cross-reactions in which the antibody reacts with antigens other than those specific antigens for which the test is to be performed. Reduced sensitivity in this type of immunoassay gave rise to the use of monoclonal antibodies which do not exhibit broad cross-reactivity and thus do not generally give false negative results.

The techniques for obtaining monoclonal antibodies useful in the immunoassay techniques of the present invention are derived from the techniques first described by Milstein and Kohler and reported in Nature 256, 495–497 (1975). The formation of a hybridoma permits production of large quantities of a monoclonal antibody which is the product of a single cell line.

In a living organism, the introduction of an antigen triggers the production of the host's immune system. The immune system responds by producing a series of antibodies to all recognizable sites or determinants on the antigen. Hybridomas can be screened first to determine those which produce antibodies to combat the specific antigen. Another level of screening is possible to select a hybridoma which secretes a site-specific antibody. The hybridomas which possess the highest affinity for the immunogenic substance originally introduced are selected to provide the monoclonal antibody(ies) for some of the immunoassay techniques utilized in conjunction with the subject invention. Further screens can be run on these monoclonal antibodies to identify those antibodies which cross react. By eliminating these cross-reactive monoclonal antibodies, the occurrence of false negative test results can be minimized.

Since the sandwich immunoassay relies upon the formation of an antibody-antigen-antibody-solid surface sandwich, typically two different monoclonal antibodies which do not interfere with the binding of each other to the antigen are selected to be the antibody bound to the solid surface. Since both antibodies are necessary to complete the sandwich, reverse and simultaneous assays can be conducted without concern that a complex of labelled antibody-antigen-labelled antibody will form, precluding the formation of a complex between the antigen and the antibody bound to the solid surface. The fact that the antibodies are specific to different antigenic sites also permits the use of a "fast forward" assay. This technique eliminates an intermediate washing step between the addition of the antibodies.

In the case of a forward assay, the same monoclonal antibody can be used for both the labelled antibody and the antibody bound to the solid support when the antigenic substance possesses identical antibody binding sites sufficiently remote from each other to allow more than one antibody molecule to be bound at the same time. In such a system the addition first of the bound antibody to the sample precludes formation of a sandwich because of steric considerations. When the labelled monoclonal antibody is subsequently added, it is also able to complex with the antigen bound to unlabelled antibody immobilized on the solid phase.

The unlabelled monoclonal antibody used in the present invention to extract the antigenic substance from the sample being tested may be immobilized on any of the common supports used in immunometric assays. Among these may be mentioned filter paper, plastic beads or test tubes made from polyethylene, polystyrene, polypropylene or other suitable material. Also useful are particulate materials such as agarose, cross-linked dextran, and other polysaccharides. The techniques for such bonding are well known to those skilled in the art. For example, antibodies may be bound to polysaccharide polymers using the process described in U.S. Pat. No. 3,645,852.

The labelled monoclonal antibody used in the present invention may be provided with the same labels used in prior art immunometric assays. Among these may be mentioned fluorogenic labels for detection by fluorimetry as described in U.S. Pat. No. 3,940,475 and enzymatic markers as described in U.S. Pat. No. 3,645,090. It is also possible to label the antibody with a radioisotope such as $I^{125}$ using, for example, the procedure of Hunter and Greenwood, Nature 144 (1962), page 945, or that of David et al., Biochemistry, Vol. 13, pp. 1014–1021, (1974).

In a typical assay, the amount of labelled antibody associated with the insoluble sandwich complex is determined by examination of the insoluble carrier material by suitable means. However, it is also possible to relate the presence or absence of antigen in the fluid sample being assayed to the amount of labelled antibody which does not react during the assay and remains in a soluble form.

Some of the specific types of immunoassays which can be performed according to the methods and apparatus of the subject invention detect the presence of HCG (human chorionic gonadotropin), IgE (immunoglobulin Type E), CEA (carcino embryonic antigen), FER (ferritin), TSH (thyroid stimulating hormone), CKMB (creatine kinase), and AFP (alphafeto protein).

Some of the immunoassay techniques which can be performed according to the methods and apparatus of the instant invention are currently available in kit form from Hybritech Incorporated, San Diego, California. In particular, some of these kits are currently marketed as Tandem®-E FER, Tandem®-E HCG and Tandem®-E TSH. Many of these kits embody the invention of U.S. Pat. No. 4,376,110 which has previously been incorporated by reference into this application. The product specifications and descriptions included with these Tandem® ImmunoEnzyMetric Assays are also incorporated by reference.

It should also be noted that although the preferred embodiment is described with reference to sandwich immunoassay techniques, and with reference to the Tandem products sold by Hybritech Inc., other immunoassay techniques can be accomplished by the methods and apparatus of the instant invention and are intended to be within the scope of this invention, even though not specifically described in this application.

B. Components of the Immunochemistry Analyzer

The Immunochemistry Analyzer is one of the preferred embodiments for the apparatus of the present invention. The Analyzer is a computer-driven batch analyzer that performs most of the laboratory operations associated with the immunoassay techniques. All operations, including pipetting, aspirating, washing and reaction-quenching are precisely timed and executed so that reproducible assay results may be obtained. All samples are measured with either a discrete wavelength spectrophotometer or a spectrofluorometer. The spectrophotometer measures the absorbance of the liquid solution of the assays with any one or two wavelengths in the range of 340–700 nanometers, and converts those readings into analytical values. The spectrofluorometer portion of the instrument measures the relative fluorescence intensity in liquid samples, and converts those readings into analytical values which may be used in various diagnostic procedures. This analyzer allows for quantitative, qualitative and ratio data reduction. Further description of the optics module is contained within an application assigned to a common assignee entitled PULSE EDITING APPARATUS AND METHODS, the relevant portions of which are hereby incorporated by reference.

It should be noted again, at this point, that although the Hybritech Immunochemistry Analyzer described herein contains two processing in one instrument, it is intended to be within the scope of this invention to provide for those two stations in different instruments.

The Immunochemistry Analyzer is comprised of two major components. First, there is the sample processor unit which houses the sample processor module, the reaction processor module and the optics module. The second major component is the automatic controller, in this embodiment an IBM personal computer which guides the operator through the steps of running the assay, calculates the data and controls the internal robotics of the sample processor and reaction processor modules.

1. The Sample Processor Module

The sample processor module has two probes that aspirate and dispense sample and conjugate liquids into the appropriate reaction tubes in controlled volumes. These probes are washed whenever sample and conjugate are dispensed, thereby minimizing carryover from sample to sample, minimizing test "noise" levels.

Typically, the sample cups are contained in a 5×12 matrix tray positioned on one side of the sample processor module. The reaction tubes are held on the other side of the sample processor module in a similar 5×12 matrix rack of tubes. In this preferred embodiment, each of the reaction tubes contains a solid support, to which is bound a specific antigen or specific antibody. Other embodiments may instead rely upon binding the antigen or antibody to the tube wall itself, or in still other embodiments, may not require solid supported components at all. All of these embodiments are intended to be within the scope of this invention.

2. The Reaction Processor Module

The reaction processor module removes the unreacted sample serum/conjugate liquids, washes the beads to remove unbound labelled antibody and sample liquids, then aspirates the washed liquids and dispenses substrate reagent liquids into each tube. After substrate incubation, the reaction processor module adds quench reagent, then aspirates the solution into the optics module.

3. The Optics Module

In this preferred embodiment, the optics module measures either absorbance or fluorescence. The spectrophotometer portion of the analyzer consists of a tungsten quartz-halogen lamp, a filter wheel, a silicon detector, and the respective circuitry which allows light readings to be converted into digital readouts. Samples are aspirated into a flow cell where they may be read mono- or bi-chromatically at wavelengths between 405 and 600 nanometers.

The spectrofluorometer portion of the optics module consists of a tungsten quartz-halogen lamp, an excitation filter wheel, emission filter wheel, a photomultiplier tube and the respective circuitry which allows fluorescent readings of samples in the flow cell to be converted to a digital readout. Further details can be found in PULSE EDITING APPARATUS AND METHOD.

All wave length selection is system-controlled according to instructions entered into the assay protocol which has been stored in the memory of the automatic controller.

In this preferred embodiment, the optics module has an absorbance range of 0 to 2.5 A. The detector range is from 340 to 700 nanometers. The optics module may have polychromatic abilities, capable of reading multiple wavelengths per sample. The software which is provided with the Hybritech Immunochemistry Analyzer is designed for full operator prompting of the optics module.

4. The Automatic Controller

The automatic controller preferred for use in the Hybritech Immunochemistry Analyzer is the IBM Personal Computer. The components of the IBM Personal Computer are more fully described and understood with reference to the IBM Guide to Operations Manual, which is typically provided with each IBM-PC and the contents of which are hereby incorporated by reference in this application.

Screen Format

All screen displays are divided into three parts. The top three lines of the screen give the screen title, the system date and the time. The mid-section of the screen displays information specific to the function of the screen. Appearing along the bottom of this section is a bulletin which carries warning messages, error messages or general information. These bulletins can be cleared either by the correction of an error condition when an error is indicated, or by the next keyboard entry. The lower section of the screen displays prompts for the operator and the function key assignments.

The function keys are defined by the specific software and are used to enter both commands and data. Commands appear on the screen when they can be immediately carried out by the operator. The operator presses the function key to execute these commands. Commands with irreversible results, such as deleting a protocol or a run, always require confirmation.

System Menu

The main commands which are available in the software provided with the Hybritech Immunochemistry Analyzer are shown in the menu of FIG. 1. Once a main command (one of the six boxes appearing at the top of FIG. 1) has been selected, one of its subsequent steps (subtended from the "main command" boxes) may be selected individually.

The MAIN COMMAND screen shown in FIG. 2 is the first screen displayed when the Immunochemistry Analyzer is reset. It is also displayed in response to the function key, FO MAIN COMMANDS, which appears on all other system screens. The MAIN COMMANDS screen displays the run status on both the sample processor and the reaction processor with the following indicators.

Initializing: The information from the floppy disc is being loaded by the IBM PC.
Ready: The processor is empty and waiting for a run.
Starting: The processor is waiting for operator confirmation of the start command.
Stopped: The stop command has been given and confirmed.
Running: Assay is started, but is not completed.
Finished: The assay is completed.
Shutting down: The processor is going through its mechanical shutdown process of washing the feeder tubes and the flow cell.

As shown in the output displayed in FIG. 2, the system displays a processing message over the run and rack positions on the sample processor side of the MAIN COMMANDS screen whenever the sample processor is mechanically activated. On the reaction processor side of the screen, one of five processing messages may be displayed, depending on the stage of the assay. These messages are: priming, washing, incubating, quenching and reading. When the wash and quench reagent reservoirs are full, the message OK is displayed within the "wash" and "quench" fields of the MAIN COMMANDS screen. When the supply in either reservoir is low, the OK message is replaced by a low indicator, in this embodiment, a flashing cursor that prompts the operator to add wash or quench reagents. The OK message is also displayed within the "waste" field until the waste container is filled. When it is filled, the OK message is replaced by an intensified blinking block that indicates the container must be emptied.

Assay Selection and Protocol

The assay selection and protocol functions allow the operator to select, view, add, modify, copy, delete or rename an assay protocol. To access the ASSAY SELECTION PROTOCOL screen as shown in FIG. 3, the function key F6 is depressed when the MAIN COMMAND screen of FIG. 2 is displayed. An on-line list of existing and entered assay protocols is displayed on the ASSAY SELECTION screen, shown more clearly in FIG. 3.

To add a protocol to this list, the F2 key is depressed. This brings up the ADD PROTOCOL screen shown in FIG. 4. The list of on-line protocols remains displayed and the next available protocol space is highlighted. Two options are given at this point, F9 HELP or F0 ABANDON ADD PROTOCOL. These function keys permit immediate exit from the "add protocol" subroutine.

To continue with the "add protocol" subroutine, type in the name of the protocol to be added using up to sixteen alphanumeric characters to identify the protocol. The operator next selects the mode of operation associated with the added protocol. F1 FULL INSTRUMENT PROCESSING can be selected if both sample and reaction processing are required. F3 READ/CALCULATE PROCESSING can be selected to use the spectrophotometer part of the optics module to measure the absorbance of enzymetric immunoassays produced by manufacturers other than Hybritech, Inc.

When F1 FULL INSTRUMENT PROCESSING is chosen, the display screen prompts the operator to add protocol parameters as shown in FIG. 5. The system prompts the operator for input of the length of the first incubation period. Once the correct incubation period has been entered, the return key is entered. The system then prompts for the length of a second incubation period. The operator enters the correct time period and presses the return key. Next the cursor moves to addition order for sample processing. Three options are assigned to the function keys F1(bead/sample/conjugate), F3 (bead/conjugate/sample), and F5 (sample/bead/conjugate). The operator selects one of these three options and continues to complete protocol parameter entering.

Next this ADD PROTOCOL screen prompts for the number of calibrators and the number of controls to be run for this added protocol. The operator may enter up to six calibrators and up to five controls. This ADD PROTOCOL screen also prompts for the sample volume and conjugate volume for the new protocol. The operator enters the appropriate volume of sample and conjugate needed for processing the sample and then presses the return key. The ADD PROTOCOL screen shown in FIG. 5 also prompts for the "curve type", a parameter related to the quantitative data reduction methods to be used according to the new protocol. The types of curves which may be selected are linear, point-to-point, polygonal, qualitative, ratio and diagnostic ratio.

This ADD PROTOCOL screen, shown in FIG. 5, prompts for the units of concentration to be recorded in the protocol. The "optics mode" field is also displayed on the ADD PROTOCOL screen. Function keys F1 (absorbance) and F3 (fluorescence) may be selected by the operator. If "absorbance" is selected, the operator is prompted for absorbance primary and secondary wavelengths. The primary wavelength is the wavelength at which the chromophore is typically read. The secondary wavelength allows unknown samples with absorbances greater than about 2.2 A at the primary wavelength to be interpolated from the secondary wavelength standard curve. There may be up to twelve choices for both primary or secondary wavelengths. These options are offered on the function keys as follows:

F5 is 360 nanometers
F7 is 405 nanometers
F4 provides more choices.

If F4 is selected, then F1 may correspond to 450 nanometers, F3 to 490 nanometers, F5 to 550 nanometers and F7 to 600 nanometers.

When "fluorescence" is chosen, the instrument prompts for excitation and emission wavelengths. The options offered on the function keys are F5=360 nanometers, F7=405 nanometers, F4=more choices. The additional choices may be, e.g., F1 as 450 nanometers, F3 as 490 nanometers and F5 as 580 nanometers.

When the operator has entered all the parameters on the first ADD/PROTOCOL screen shown in FIG. 5, the controller changes to a third ADD PROTOCOL screen which prompts for values and ranges for the new protocol as shown in FIG. 6. Each parameter which must be defined for the new protocol is highlighted on the third ADD PROTOCOL screen. The operator enters values for each calibrator, and then specifies the number of calibrator replicates. The operator also specifies the low and high for the controls and the reference range for the patient's sample. The return key is entered after each entry. To delete parameters, position the cursor in the appropriate field and then select F2. Once the information has been deleted new parameters may be entered. To delete the parameters and return to the MAIN COMMANDS screen, press F0 ABANDON CHANGES MADE TO PROTOCOL. F6 MODIFY PROTOCOL can be selected to change specific parameters. F8 STORE ALTERED PROTOCAL can be selected to store the parameters which have been entered for the protocol.

To use the Immunochemistry Analyzer as a spectrophotometer, the operator selects F3 on any of the ADD PROTOCOL screens (FIGS. 4, 5 and 6). This brings up the fourth ADD PROTOCOL screen (Read/Calculate Processing) which is shown in FIG. 7. The system prompts for those assay parameters necessary for measuring the absorbance of samples and analyzing the data. Enter the new parameters, then store the protocol (F8), delete the protocol (F0) or modify the protocol (F6).

Set-Up/Start Trays

The ASSAY SELECTION screen shown in FIG. 8 may be accessed from the MAIN COMMANDS screen by selecting F2. This ASSAY SELECTION screen displays the runs in progress and shows which tray of a run is currently being processed in the sample processor. Using the function keys which are displayed on this screen, the operator can delete a run in progress and all references to that run, stop the tray currently being processed, set-up a new tray, or start a new tray.

To begin a new run, F1 SET-UP TRAY(S) is selected from the ASSAY SELECTION screen shown in FIG. 8. F1 brings up the SET-UP/START TRAY(S)

screen shown in FIG. 9. A menu of the existing protocols is displayed. The operator can move the cursor to selected a protocol and then press F1 ENTER # OF TRAYS to enter the number of trays to be run. The screen prompts the operator to specify the number of trays to be used in that run. The correct number is entered and the return key is pressed. The screen allocates the trays in sequence beginning with 1.

After this sequence the controller brings up a second SET-UP/START TRAY screen as shown in FIG. 10. An array of 60 positions in the first tray is displayed on the screen as shown in FIG. 10. The new trays are initialized to the protocol specifications, i.e., the first two positions are reserved for calibrators and controls specified in the protocol (see above, particularly, FIGS. 5, 6 and 7). The position of the cursor indicates the first sample number, and the system prompts "manually enter sample I.D.'s or select function". If the operator opts to manually identify the samples, he/she keys in an identifier of up to twelve alpha-numeric characters and then enters the identification by pressing the return key. Each individual sample must be identified. If the operator selects F1 ASSIGN AUTO IDS, then the controller automatically assigns sequential identification numbers.

Start Tray

The operator selects F4 START TRAY (on any SET-UP/START TRAY SCREEN, see, e.g., FIGS. 9 and 10) when ready to run the assay. This brings up the START-TRAY screen shown in FIG. 11. The system prompts the operator to insert the tray of patient samples and a rack of reaction tubes into the sample processor unit and to insert a bottle of conjugate into the conjugate/substrate receptacle. The operator places the sample tray and reaction tube rack on the sample processor shelf with the disc identifier of the reaction tube rack on the far right.

The disc identifier is more clearly shown in FIGS. 12a and 12b. Each reaction tube rack 10 contains twelve circular openings 22, 24, etc. on one side wall 28 of the rack. The disc identifier 26 is a reflective button which snugly fits into the circular openings, e.g., 22, and is secured therein by means of sprues 30. These sprues 30 contract to fit through the openings but expand to keep the disc 26 in place. The disc identifier is positioned in one of twelve circular openings in the sidewall 28 of the individual rack 10 to be identified.

Due to its reflective properties, the position of the disc identifier 26 can be optically sensed by the system (automatic controller) which then is able to associate the particular assay technique to be run on that rack with the position of the disc 26. When the operator loads a reaction tube rack to either the sample processor module or the reaction processor module, the location of the disc 26 is optically detected. If the operator seeks to perform assay steps incompatible with the location of the disc 26, the system prompts the operator that an error has been detected and must be corrected before additional procedures are accomplished.

This preferred embodiment of the reaction tube rack and disc identifier is described with reference to a reflective button which can be located in one of twelve positions. However, the invention described and claimed herein concerns the steps of uniquely identifying each rack, and subsequently verifying the identification of each rack by the automatic controller. Other embodiments which accomplish these steps are possible and are intended to be within the scope of this invention.

When the sample tray and the reaction tube rack have been loaded to the sample processor shelf, the operator selects F6 CONTINUE START and receives the following prompt: "Replace conjugate bottle with an empty bottle, then press F6". When the empty conjugate bottle is in position and F6 is pressed, another prompt appears on the screen: "Washing conjugate lines, please wait". When the conjugate lines have been washed, the system again prompts: "Put new conjugate bottle into instrument, then press F6". After the new conjugate bottle has been inserted, the system starts sample processing. The screen switches to a MAIN COMMAND screen as shown in FIG. 13 displaying which operations are taking place in both the sample processor module and the reaction processor module.

Wash/Read a Rack

From the MAIN COMMAND screen the operator can select F4 WASH/READ A RACK to access the WASH/READ A RACK screen shown in FIG. 14. This screen lists the runs currently in progress. The runs are either set-up and awaiting sample processing, in sample processing, finished sample processing, incubating, being washed, being read or finished. From this screen the operator can manipulate the calibration curves, delete runs, start runs or stop runs.

From the WASH/READ RACK, F4 (START RACK) is selected. A START RACK screen is displayed in FIG. 15. The START RACK screen lists the rack that the operator selected to run, and prompts the operator to place the reaction tube rack in the reaction processor. Selecting F6 CONTINUE START provides further instructions. Once the operator has ascertained that there is sufficient wash solution in the instrument to perform the assay bead washing as specified in the particular assay kit, the operator selects F6 CONTINUE START and the computer starts the reaction processing. The system returns to the MAIN COMMAND screen which now indicates that the reaction processor is in use. This is shown in FIG. 16.

Retrieve Results

The RETRIEVE RESULTS screen can be accessed from the MAIN COMMAND screen by selecting F3 RETRIEVE RESULTS. This screen, as shown in FIG. 17, allows the operator to retrieve reports of patient and control results, including quality control statistics. Additionally, it allows the operator to change or modify the headings of the report and to automatically print operator-entered data and the system responds. Both on-line and stored results are accessible to the operator through the RETRIEVE RESULTS screen. However, if no data is entered for this assay run, a bulletin reports that no results have been stored on the analyzer.

C. Robotics of the Sample Processor Module and the Reaction Processor Module

1. Sample Processor Module

FIG. 18 is a top view of the sample processor module. A sample tray 50 is a 5×12 matrix of sample cups 52 containing the sample serum to be analyzed by immunoassay techniques. A carriage 54 is located in the middle of the sample processor module. The sample tray 50 is placed on a moving shelf (not shown in this view) which causes the tray 50 to move discretely, in increments equivalent to the distance between the centers of sample cups 52 one row apart. Thus, in twelve separate movements the tray 50 is moved from the position indicated by the solid lines to the position indicated by the broken lines.

Subtended from the carriage 54 is a probe assembly 56 which can move vertically to insert and to extract a sample aspirator 58 and conjugate dispenser 59 from the sample cups 52. On the sample tray 50 side of the sample processor module, the sample aspirator 58 aspirates a preset volume of sample serum from the cup 52 and maintains the aspirated fluid in the probe assembly 56. On the other side of the sample processor module is a reaction tube rack 60, comprising a second 5×12 matrix of reaction tubes 62. In this preferred embodiment, the reaction tubes 62 contain a solid support bead, more clearly shown and described with reference to FIG. 19, below. After the sample aspirator 58 has aspirated sample fluid, the carriage 54 moves the entire probe assembly 56 to the reaction tube rack 60 side and selects a particular reaction tube. The reaction tube rack 60 configuration is not necessarily in one to one correspondence with the arrangement of samples in the sample tray 50. This arises due to performing multiple runs of the same sample.

Once the assembly 56 is located above the appropriate reaction tube, the assembly moves down onto the tube and the aspirator 58 and dispenser 59 are inserted into the tube. Next, the sample fluid is dispensed into the reaction tube which is followed by the dispensing of a first reagent. The immunochemical importance of the solid support and the reagents have been set forth in prior sections of this description.

The end view shown in FIG. 19 depicts some of the important dimensional relationships in the sample processor module. The sample tray 70 contains sample cups 72 which are not nearly as deep as the reaction tubes. This permits the conjugate dispenser 74 to stay above the liquid level in the sample cup 72. The aspirator 76, however, is long enough to reach into the sample cup 72 and aspirate the sample fluid. The entire probe assembly 78 then moves across to the other side of the sample processor module by action of the carriage 80. The assembly 78 focuses in upon a reaction tube 82 held in place by the reaction tube rack 84. A solid support 86 is contained within the reaction tube 82, and is part of the immunochemical system of the assay technique.

In between the sample tray 70 and the reaction tube rack 84 is a probe washing station 88. Once the probe assembly 78 has completed dispensing sample serum and conjugate into the reaction tube 82, the carriage 80 moves the assembly to the probe wash station 88 where the sample aspirator 76 and conjugate dispenser 74 are washed prior to their exposure to the next sample cup. This three step process of aspirating sample from a sample cup, dispensing sample fluid and conjugate in the reaction tube and washing the probe is repeated row by row column by column until all sample fluids have been transferred to the reaction rack side of the sample processor module.

The intermediate washing of the probe assembly is required to prevent cross-contamination between samples. Due to the extreme sensitivity of immunoassay techniques, careful washing of the sample aspirator and conjugate dispenser is important. The probe wash station is the subject of a separate application assigned to a common assignee entitled PROBE WASH STATION. FIG. 20 illustrates the probe wash station 90 and the probe assembly 92. The probe assembly 92 is lowered into the probe wash station 90. The sample aspirator 94 descends into a cylindrical cavity 95. The conjugate dispenser 96 is not quite as long. Electrodes 98 and 100 are radially disposed about the assembly 92 at a distance further from the center of the assembly 92. The wash cup 101 has a shelf 102 which is adapted to receive the electrodes 98 and 100. The wash cup 101 is contained within a larger cylindrical cavity 104. When the wash fluid flows out of the cup 101, a drain 106 removes the excess fluid.

FIG. 21 illustrates the washing step. Washing fluid is dispensed through the sample aspirator 94. The fluid fills the cylindrical cavity 108 and flows over the shelf 102 into the cylinder 104. The outlet 106 is connected to an aspirator through tube 108. Since the conjugate dispenser 96 is of a length designed to keep it above the fluid level in either the sample cup or reaction tube, it does not have to be as thoroughly washed s the other probes on each cycle since the cross-contamination problem is not as critical for that probe.

2. Reaction Processor Module

Figure 22:
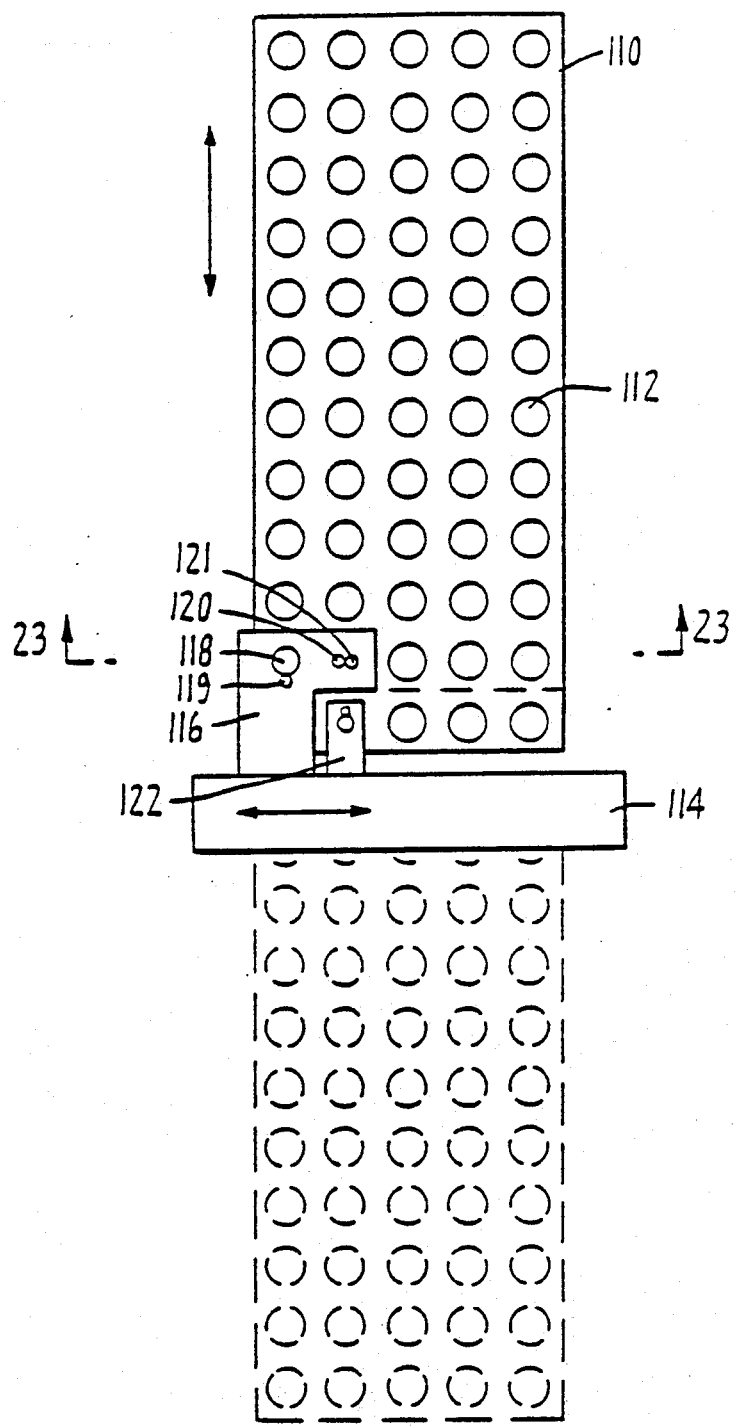
FIG. 22 is a top view of the reaction processor module.
Figure 23:
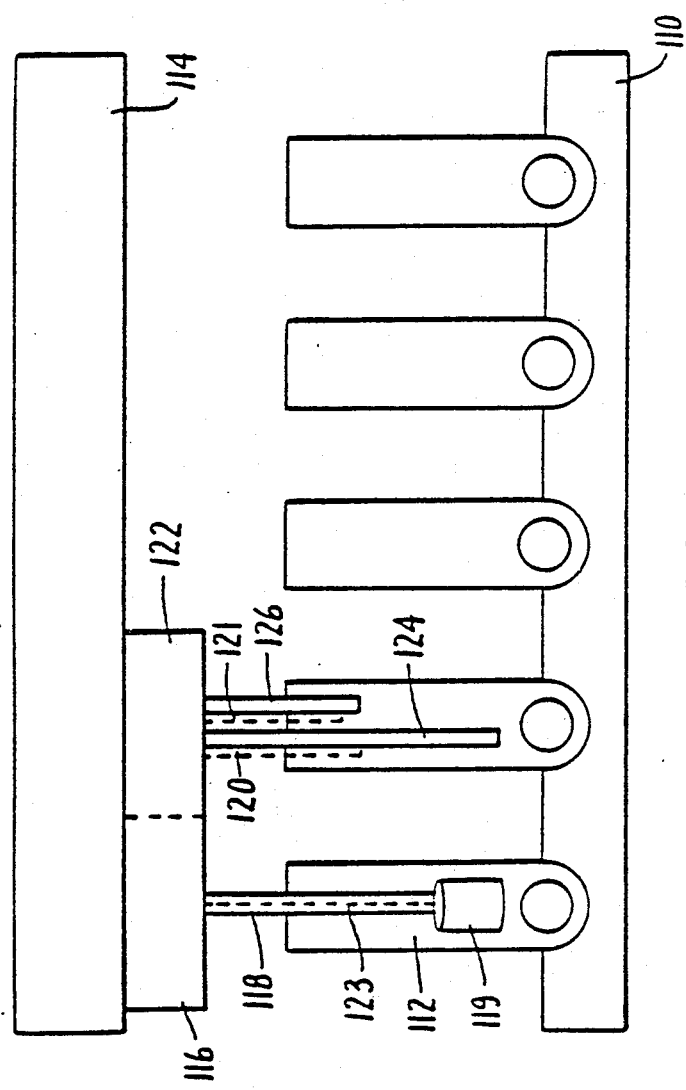
FIG. 23 is an end view of the reaction processor module, including a bead wash probe and a diluent probe.

After the reaction tubes have been incubated for a period of time, the rack of reaction tubes is placed on the reaction processor module shown in FIGS. 22 and 23 for further processing. The reaction processor module also contains a probe which aspirates, e.g., the chromophore-containing solution and transfers the solution to the optics module where absorbance or fluorescence are measured.

In FIG. 22, the reaction rack 110 contains sixty reaction tubes 112 configured in a 5×12 matrix. Again, the rack 110 is supported on a platform which moves in discrete distances perpendicular to a carriage 114 which supports a reaction probe assembly 116. The reaction probe assembly carries a wash-aspirating probe 118, a detergent-adding probe 119, a substrate probe 120 and a diluent/quench probe 121. Offset from, but proximate to the reaction probe assembly is an optics module aspirator 122 which enables transfer of the reaction solution to and from the optics module to determine abosrbance or fluorescence, returning the solution to the reaction tube subsequent to the reading step.

Immunoassay techniques require the removal of unreacted sample and reagent components prior to the substrate reaction. This washing step must be good to the parts per million level to assure assay accuracy and precision. The Immunochemistry Analyzer contains several features which enable automation of this important washing step heretofore unknown. In particular, the reaction probe assembly and wash probe are described in more complete detail in a separate application entitled TUBE TRAP APPARATUS, assigned to a common assignee. Further, the automation of the wash steps is described and claimed in my application entitled BEAD WASHING METHOD AND APPARATUS, also commonly assigned.

The various probe assemblies are more clearly described with reference to FIG. 23. The reaction probe assembly 116 is subtended from the carriage 114. The wash probe 118 (shown in further detail in FIG. 24 and FIG. 25) has an enlarged terminus 119 which permits the removal of large volumes of washing fluids in a short interval of time. The detergent-adding probe 123 introduces detergent solution to the reaction tube during the wash cycle. Substrate probe 120 and a quench dispenser 121 are also subtended from assembly 116. The substrate probe 120 and quench dispenser 121 are offset from the wash probe 118 so that they would typically be located over the next succeeding reaction tube in the same row as the wash probe.

The optics module aspirator 122 comprises a first probe 124 which aspirates fluid out of a reaction tube and a second probe 126 for returning fluid to the same reaction tube. The aspirator 122 is joined to a flow cell (not shown here) within the optics module of the Immunochemistry Analyzer permitting either spectrophotometric or spectrofluorometric analysis of the reaction tube solution.

Figure 24:
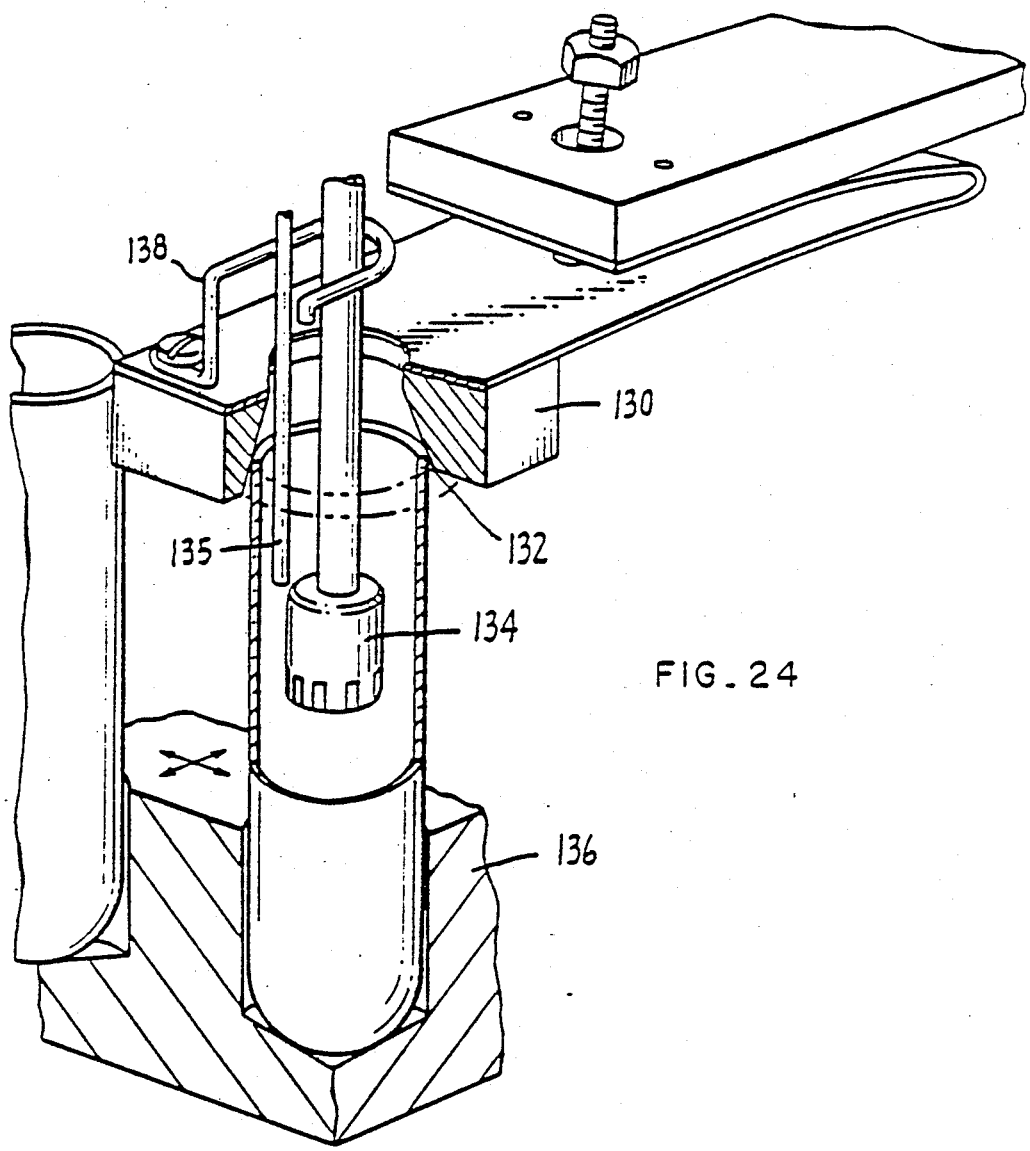
FIG. 24 is a perspective view of a wash probe and tube trap assembly.
Figure 25:
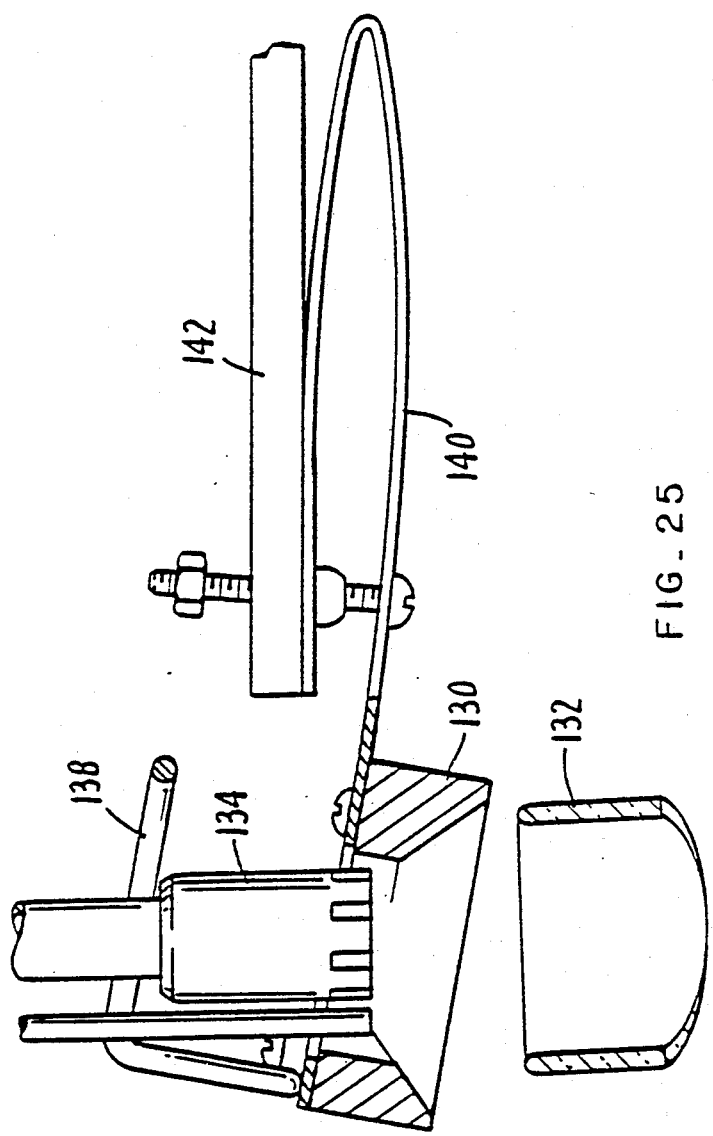
FIG. 25 is a side cross section view of the bead wash probe and tube trap assembly.

FIG. 24 shows the tube trap assembly and wash probe which are described and claimed in the application entitled TUBE TRAP APPARATUS. Briefly, the frustoconical shape of the tube trap 130 is selected to focus the top of the reaction tube 132 prior to the insertion of wash probe 134. Since the diameter of the reaction tube 132 and the probe 134 are so close, accuracy of the insertion was required to prevent the probe 134 from hanging up on the tube top 132. The tube rack 136 was not capable of this level of accuracy. Detergent-adding probe 135 also is shown in FIG. 24. The use of two probes to accomplish addition and removal of the detergent fluids makes the wash cycle time shorter.

When the probe 134 is removed from the tube 132, a bail 138 catches the probe 134 and moves the tube trap 130 up and away from the tube top 132. This is more clearly shown in FIG. 25 which illustrates a withdrawn probe 134 pulling the trap 130 away from the tube 132. The U-spring 140 is sufficiently flexible to permit a deflection of this magnitude. The entire tube trap apparatus is connected to the carriage 142.

While the subject invention has been described with reference to a preferred embodiment, it will apparent that other changes and modifications could be made by one skilled in the art, without varying from the scope or spirit of the claims appended hereto.

We claim:

1. A method for automatically performing immunoassay techniques on a rack of reaction tubes, the method comprising the steps of:
   identifying uniquely a rack of reaction tubes;
   communicating to an automatic controller the immunoassay technique to be performed on said rack of reaction tubes;
   automatically communicating to the controller the unique identity of said rack;
   loading the rack to a first station;
   I. at the first station, according to the particular immunoassay technique selected,
      (a) automatically adding sample serum to each of said reaction tubes to permit the sample serum to contact a substance which will immunochemically bond to a specific immunogenic component of said sample serum;
      (b) automatically adding a first reagent to said reaction tubes which reagent also immunochemically bonds to said specific immunogenic component of the sample serum to form a first complex;
      (c) removing said rack of reaction tubes from the first station;
      incubating said reaction tubes for a first period of time;
      loading the rack to a second station;
      automatically verifying by said controller the unique identity of said rack; and
   II. at the second station, according to the particular immunoassay technique originally selected,
      (a) automatically washing away unreacted components of the sample serum and reagents in each reaction tube to leave said first complex;
      (b) automatically adding a second reagent to said washed reaction tubes which second reagent results in the formation of an optically detectable substance;
      (c) incubating the rack of reaction tubes for a second period of time;
      (d) automatically adding a diluent and/or a quenching reagent to said reaction tubes; and
      (e) automatically transferring the contents of each reaction tube to an optics module; and
      (f) obtaining and presenting an optical characterization of the contents of each of said reaction tubes.

2. The method of claim 1 wherein the substance of step I (a) binds to a solid support.

3. The method of claim 1 wherein the substance of step I, (a) is a monoclonal antibody.

4. The method of claim 1 wherein the specific immunogenic component of step I, (a) is a specific antigen.

5. The method of claim 1 wherein the second reagent of step II, (b) is a chromophore-forming substrate which is activated in the presence of the first reagent.

6. The method of claim 1 wherein an additional step of communicating with the controller to determine when the first incubation period will end is performed after beginning the first incubation period for said reaction tubes.

7. The method of claim 1 wherein said controller comprised, in part, interactive components and memory storage.

8. The method of claim 1 wherein said rack identifying and verifying steps comprise using an optical marker on the rack of reaction tubes and automatically, optically sensing the marker.

9. The method of claim 1 wherein the step of obtaining and presenting an optical characterization of the contents of each of said reaction tubes is performed by an optics module.

10. An apparatus for automatically performing immunoassay techniques on a rack of reaction tubes, which comprises:
   (a) means for identifying uniquely a rack of reaction tubes;
   (b) an automatic controller;
   (c) means for automatically communicating to the controller the unique identity of said rack;
   (d) a first station;
   (e) means for automatically adding sample serum to each of said reaction tubes;
   (f) means for automatically adding a first reagent to said reaction tubes;
   (g) means for automatically verifying by said controller the unique identity of said rack;
   (h) a second station;
   (i) means for automatically washing away unreacted components of the sample serum and reagents in each reaction tube to leave said first complex;
   (j) means for automatically adding a second reagent to said washed reaction tubes;
   (k) automatically adding a diluent and/or quench reagent to said reaction tubes;
   (l) an optics module;
   (m) means for automatically transferring the contents of each reaction tube to an optics module; and (n) obtaining and presenting an optical characterization of the contents of each of said reaction tubes.

11. The apparatus of claim 10 wherein said controller comprises, in part, interactive components and memory storage.

12. The apparatus of claim 10 wherein said rack identifying means comprises an optical marker located on one side of the rack of reaction tubes.

13. The apparatus of claim 10 wherein said automatic rack verifying means comprises an optical sensor which is capable of identifying locations of an optical marker on the rack.

14. The apparatus of claim 10 wherein said optics module comprises a spectrophotometer.

15. The apparatus of claim 10 wherein said optics module comprises a spectrofluorometer.

* * * * *